United States Patent
Tayebi et al.

[11] Patent Number: 5,807,271
[45] Date of Patent: Sep. 15, 1998

[54] FETAL HEARTBEAT AND UTERINE CONTRACTION

[76] Inventors: Sean Tayebi, 2 Bay Club Dr., Apt. 9G-E, Flushing, N.Y. 11360; Farid Souluer, 10818 Caminito Alvarez, San Diego, Calif. 92126; Surinder Tayebi, 5240 Fiore Ter., Apt. J403, San Diego, Calif. 92122; Jalil Tayebi, 9725 Scranton Rd., No. 140, San Diego, Calif. 92121; Massih K. Tayebi, 7190-B Calabria Ct.; Masood K. Tayebi, 5240 Fiore Ter., Apt. J403, both of San Diego, Calif. 92122

[21] Appl. No.: 843,233

[22] Filed: Apr. 14, 1997

[51] Int. Cl.$^6$ ........................................... A61B 8/02
[52] U.S. Cl. ................................................. 600/511
[58] Field of Search ...................... 600/460, 511, 600/591; 128/903

[56] References Cited

U.S. PATENT DOCUMENTS

| | | | |
|---|---|---|---|
| 3,561,430 | 2/1971 | Filler, Jr. et al. | 600/453 |
| 4,781,200 | 11/1988 | Baker | 600/511 |
| 4,989,615 | 2/1991 | Hochberg | 600/591 |
| 5,431,171 | 7/1995 | Harrison et al. | 600/511 |

*Primary Examiner*—William E. Kamm
*Attorney, Agent, or Firm*—John R. Duncan; Frank D. Gilliam

[57] ABSTRACT

A monitoring system for monitoring detectable intermittent signals generated by a living being. In one embodiment, a pregnancy monitoring system monitors fetal heat beat and/or uterine contractions. A belt is configured to fit around the abdomen of a pregnant woman, with belt ends fastened together at her back. A number of sensors are mounted on the belt to detect fetal heartbeat and transmit corresponding electrical systems, preferably by wireless means, to a distant monitoring station. At least one uterine contraction sensor may also be mounted on the belt for detecting uterine contractions and transmitting a corresponding electrical signal to the monitoring station. In a second embodiment, an apron or jacket for placement in tight, uniform contact over the chest contains a plurality of sensors for detecting cardiac signals. These electrocardiographic signals are transmitted by a wireless transmitter to a distant, central monitoring system to produce a valid data signal at the remote station. Preferably, the belt and apron are in the form of a double-walled, spaced-sheet, receptacle that can be inflated, such as by an automatic air pump, to assure that the sensors are pressed tightly against the skin.

4 Claims, 2 Drawing Sheets

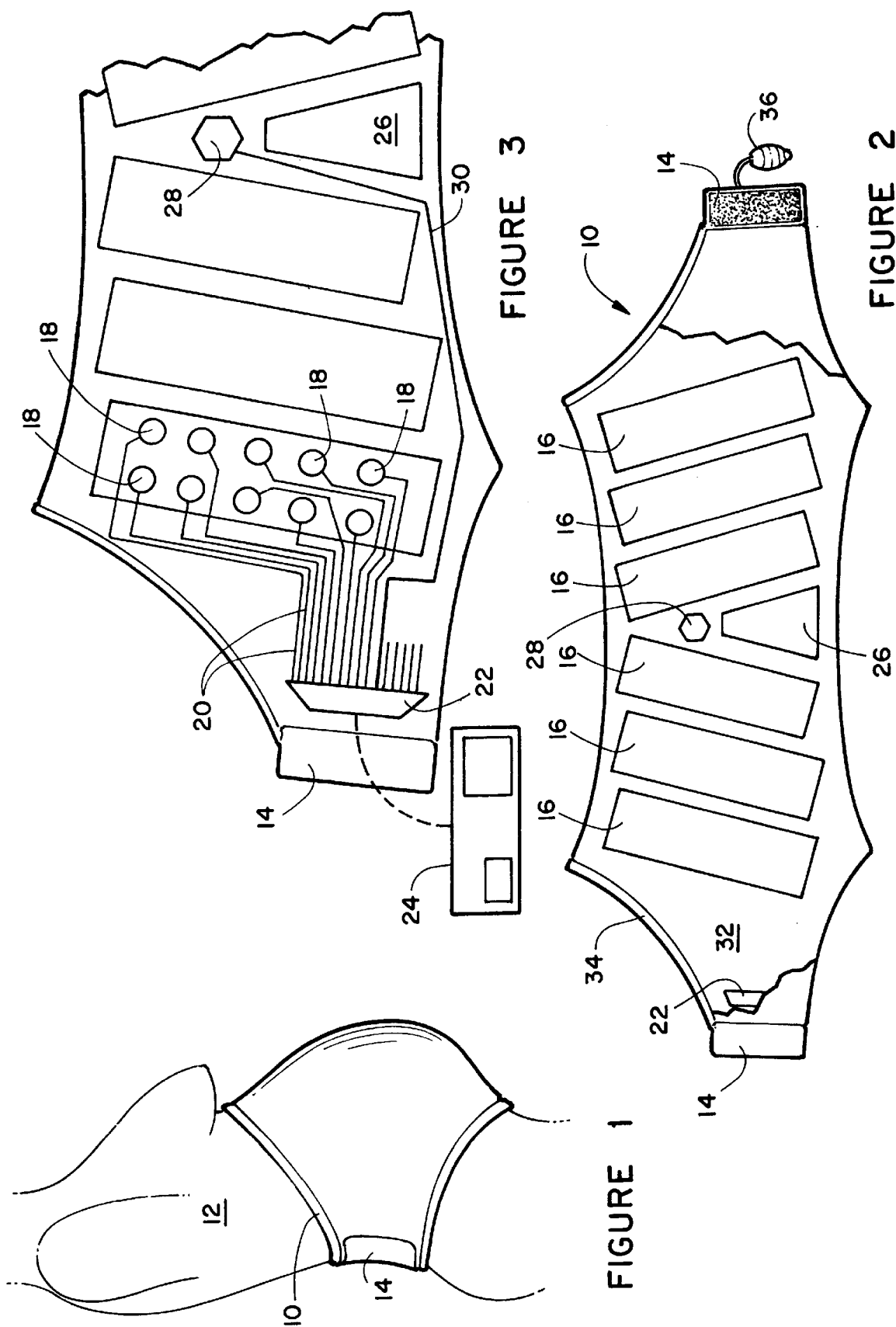

FETAL HEARTBEAT AND UTERINE CONTRACTION

FIELD OF THE INVENTION

This invention relates to external monitoring of medical information such as fetal heart beat and uterine contractions during pregnancy and electrocardiographic information.

BACKGROUND OF THE INVENTION

During pregnancy it is necessary to monitor fetal heart beat and uterine contractions to assure labor and fetal well being. Such monitoring is done from time to time during pregnancy and, in the event of actual or potential problems, may be continued for extended periods. Also, monitoring of cardiac activity for extended periods or from remote locations a long distance away is often desirable.

External monitoring of fetal heart beat requires precise placement of a Doppler transducer by trained medical personnel. This process requires careful observation by the medical staff member since the fetus may move, requiring realignment of the transducer in order to receive the desired signal signifying the fetal heart beat. The external monitoring of the fetal heart beat allows the physician to obtain a continuous reading of the fetal heart beat. A separate transducer is used to monitor uterine contractions. Fetal heart beat and contractions may be recorded on the same tracing so that a comparison can be made.

Fetal heart beat and contraction monitoring is utilized in a variety of situations during pregnancy. Monitoring is done during a normal pregnancy whenever the patient perceives decreased fetal movement to assure the well being of the baby. In addition monitoring may be done during post pregnancy as part of a biophysical profile, during labor, after a traumatic episode or during the inductive phase. In general fetal heart beat monitoring along with contraction monitoring is used whenever there is a concern regarding fetal well being.

Similarly, cardiomonitoring of individuals suffering from coronary artery disease or suspected of having coronary artery problems is important in treating this and related cardiac problems. Coronary artery disease is the leading cause of death in most of the industrialized Western world. It is a preventable disease and can be monitored, albeit indirectly, by serum chemistries and by vital signs of a patient that include the blood pressure, heart rate and respiratory rate and the core body temperature.

Electrocardiography is one of the basic elements in the monitoring and evaluation of the patient's vital statistics. Results of electrocardiographic monitoring provides a reflection not only of the patient's cardiovascular system, but also of other systems in the body. In conventional electrocardiography, the electrical impulses that stimulate the heart to contract are picked up by external(skin) sensors and recorded as an electrocardiograph. Typically, 12 separate leads are used (six limb leads and 6 chest leads. Trained medical staff examining and reading an electrocardiograph can determine the status of the person's heart and in addition other ailments that might be indirectly contributing to the person's overall cardiovascular status.

To obtain this information, one must be in a medical setting where trained personnel place the limb and chest sensors in precise locations to obtain accurate readings. This incurs considerable medical costs both to the medical office and the patient. In this setting, only short-term monitoring can be accomplished and repeated monitoring over time is difficult Monitoring of pregnancy or cardiac condition must be done in a hospital or clinical setting because of the need for continuous observation and adjustment of the sensors. This is expensive and time consuming for medical personnel and is difficult to continue for extended periods.

Thus, there is a continuing need for improved fetal heart beat and uterine contraction monitoring and for cardiac monitoring that does not require continuous observation and adjustment by medical personnel, that can be done at any suitable location and can be continued for extended periods.

SUMMARY OF THE INVENTION

The above noted problems, and others, are overcome by the pregnancy monitoring system which basically includes a body engaging continuous material, similar to a wide abdominal belt for pregnancy monitoring or a jacket or apron across the chest for cardiac monitoring, a plurality of sensors positioned in an array across the inner surface of the continuous material, means for securing the material to the appropriate body surfaces, a wireless transmitter system for transmitting signals sensed at the sensors to a central monitoring station where the signals are processed and displayed in a conventional manner for observation by trained medical personnel.

In preferred embodiments, the continuous material may comprise two spaced panels, closed along the edges to form a fluid-tight receptacle that can be inflated to cause the sensors on the sheet in contact with the body to be pressed uniformly against the body. Preferably, a large number of sensors are provided, so that the monitoring system can select signals from sensors at the desired locations, so if the sheets move or slip, changing sensor locations, the system can switch to sensors that have moved to the optimum locations.

For pregnancy monitoring, a wide belt is used, preferably sized to cover substantially the entire abdomen of a pregnant woman, including end fasteners for holding the belt in place, having a plurality of sensors on the belt for sensing fetal heart beat and uterine contractions. Transducers at each heart beat sensor convert the heart beat sound into an electrical signal. Electrical means compares the signal from different sensors and sends the most valid signal to a monitoring station. Thus, as the fetus moves, the sensor receiving the most valid heart beat signal and selected to transmit the electrical signal will change At least one additional sensor senses uterine contractions and sends an electrical signal to the monitoring station corresponding to the contractions sensed.

Preferably, the fetal heart beat sensors are grouped in panels at the right and left sides and at the center of the abdomen. The most valid signal selected automatically from a large number of sensors, typically more than 80 sensors, is then sent to the monitoring station. The uterine contraction sensor is preferably located at approximately the center of the abdomen.

For cardiac monitoring, the sheets are configured as an apron or jacket, covering the chest of the patient and extending around the sides to any desired extent. Suitable fasteners, such as straps hold the apron in place. For female patients, a suitable brassiere can be built into the apron. A plurality of conventional electrocardiograph sensors are mounted at desired locations across the apron, typically forming a basic Einthoven's triangle. A greater number of sensors that would normally be used for and EKG may be used, so that if the apron becomes misadjusted, the monitoring system can select sensors that happen to be correctly positioned. The sensors are wired to a data transmission port where signals are transmitted by any suitable wireless system to a central monitoring location.

For best results, the belt or apron is formed from two coextensive sheets secured together along the edges to form a receptacle. An automatic pump pumps fluid into the receptacle to pressurize the belt or apron. This increase the support provided to the abdomen by the belt and presses the sensors tightly against the abdomen or chest, improving signal quality. Preferably, the pressurizing fluid is air at a pressure of from about 100 grams to 1.2 kilograms per centimeter, so that the two sheets are spaced apart about 10 to 50 mm.

BRIEF DESCRIPTION OF THE DRAWINGS

Details of the invention, and of preferred embodiments thereof, will be further understood upon reference to the drawing, wherein:

FIG. 1 is a schematic side elevation view of a pregnant woman wearing the monitoring belt of this invention;

FIG. 2 is a plan view of the monitoring belt with sensor array;

FIG. 3 is detail plan view of the monitoring belt, partially cut away to show the sensor pattern and double layer configuration.

DETAILED DESCRIPTION OF PREFERRED EMBODIMENTS

Figure 6:
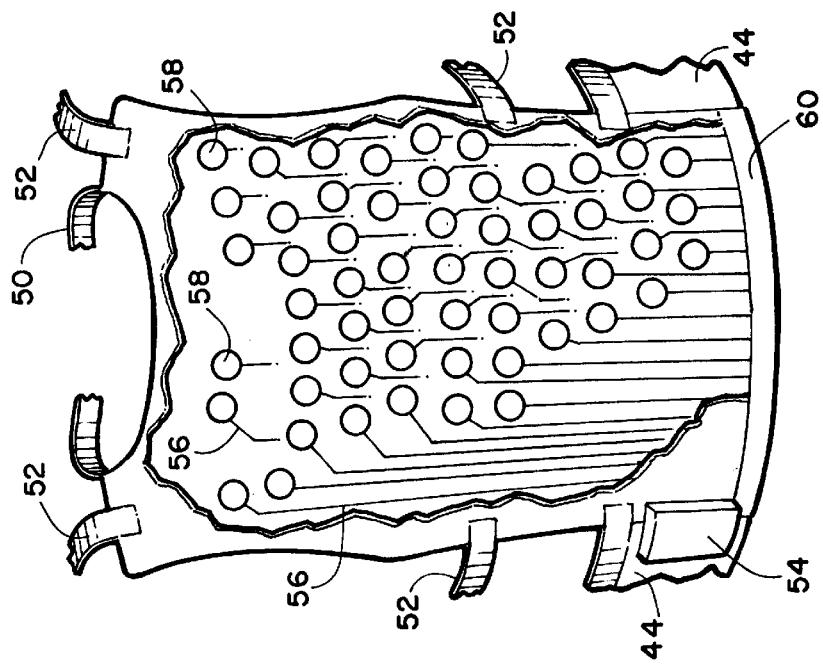
FIG. 6 is a back elevation view of the apron showing the sensor array.

As seen in FIG. 1, belt 10 is configured to cover substantially all of the abdomen of a pregnant woman 12. Belt 10 can be provided in various sizes and shapes, and is preferably formed from a stretchable, flexible material to accommodate differences in abdomen size and shape.

At the back, a fastener 14 is provided to releasably hold the ends of belt 10 together. While any suitable fastener may be used, best results are obtained with hook-and-loop fasteners of the sort available under the Velcro® trademark.

As seen in schematic plan view in FIG. 2, belt 10 has secured to the inner surface thereof a plurality of panels 16. A plurality of fetal heart beat sensors 18 are mounted on each panel 16, as best seen in FIG. 3. Each sensor 18 contains a transducer that detects heart beat sounds and transmits a corresponding electrical signal along a wire 20 to a data transmission system 22. The transducers are similar to a conventional condenser microphone, detecting sound and passing on a corresponding electrical signal. Typical such sensors are available from various sources, such as Radio Shack under the 270-090 model designation.

The data transmission system 22 receives all of the signals from all of the sensors on panels 16. A monitoring station 24 receives appropriate signals from data transmission system 22 and provides visible displays in any desired manner, such as on a CRT display, computer monitor, as paper printout, curves of data, etc.

Signals from data transmission system 22 are conveyed to monitoring station 24 in any suitable manner. While these components could be hard wired, generally a wireless system is preferred, which can use a dedicated radio system, a cellular telephone system, etc. An alarm may be provided so that when the data received is out of tolerance (e.g., fetal heartbeat slows significantly) an alarm can be sounded.

While signals from all sensors 18 could be transmitted to monitoring station 24, generally it is preferred that only the most valid signal be sent, since that is the sensor closest to the fetal heart. Data transmission system 22 selects and transmits the electrical signal which has been identified as a valid signal for fetal heartbeat. In some cases, it will be desired that the most valid signal from each of the three leftmost panels 16, from the sensor panels 16 and the central panel 26 be transmitted to assure full coverage. Any other desired pattern may be used.

Preferably uterine contractions are also be sensed at sensor 28 and transmitted to monitor 24 via wire 30 and data transmission system 22. Any suitable sensor that senses contractions and generates a corresponding electrical signal may be used. Typical of such sensors are the contraction sensors available from the Hewlett-Packard company.

In order to assure that the various sensors are pressed tightly against the abdominal skin and to give added support to the abdomen, preferably belt is formed from two coextensive sheets 32 of fluid impervious material. The sheets 32 are sealed around edges 34 to form an inflatable receptacle between the sheets. While any suitable inflating media and mechanism may be used, air is preferred as most convenient. A small battery powered automatic air pump 36 may be used to inflate the belt to a predetermined pressure. Preferably, the belt is inflated to about 100 grams to 1.2 kilograms per centimeter, so that the two sheets are generally parallel and about 10 to 50 mm apart.

Figure 4:
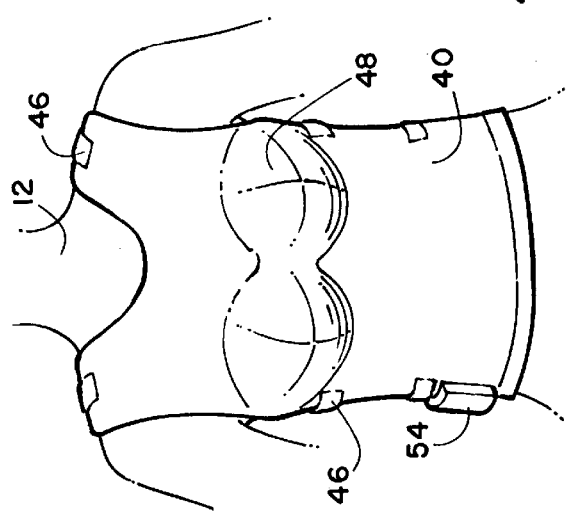
FIG. 4 is a front perspective view of the cardiac apron embodiment as worn by a female person.

The cardiac monitoring embodiment is shown in FIGS. 4–7. As seen in FIG. 4, apron 40 covers the upper front torso of person 42, extending around the sides to the extent desired. Apron 40 is held in place by a plurality of adjustable straps fastened to apron 42 at connection points 46. Where person 42 is female, a brasserie 48 is included in the apron. Bra 48 could simply comprise pockets of high stretch material, or could be more fitted, requiring different aprons to fit different persons.

Figure 5:
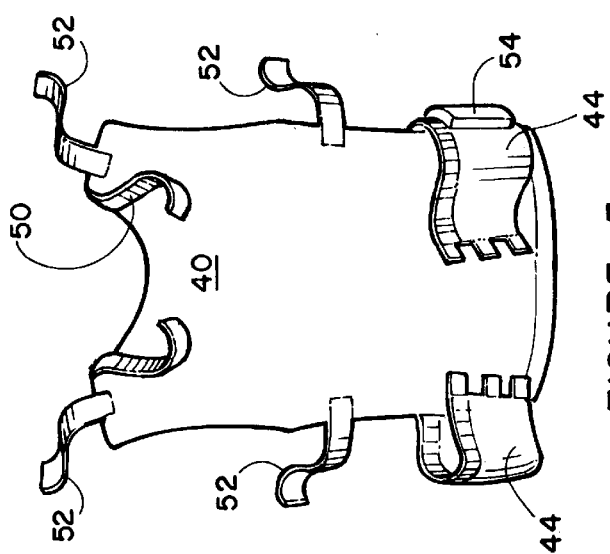
FIG. 5 is a front elevation view of the cardiac apron showing the fastening means.

As seen in FIG. 5, straps 44 preferably include a wide, belt-like strap 44 extendable around the lower torso, a narrow strap 50 extending around the person's neck 52, and such straps 54 extending over the shoulders or around the upper torso as may be desirable.

A data port 54 is secured to belt-like strap 44 and is connected by a wire 56 to each of sensors 58, as seen in FIG. 6. Wires 56 preferably extend from each sensors to lower edge band 58, where they are ganged and extend to data port 54. Data port 54 is a conventional wireless transmitter for transmitting signals from sensors 58 to a conventional central monitoring system (not shown). Any suitable transmitter and monitor system may be used. Typically, transmissions may be by conventional radio, cellular telephone systems, to a pager-like device where an abnormal signal can sound an alarm, etc. While only a single sensor may be provide at each of the conventional EKG locations, namely, at the right and left second intercostal spaces, the left fifth intercostal space under the nipple, in the fourth intercostal space and in the fifth intercostal space at the anterior and mid axillary lines. However, for optimum performance, especially where a patient will be donning and removing apron 40 from time to time and may not always precisely align the apron, preferably a much larger number of sensors 58 are provided with several around each optimum location. Then, the monitoring system may select those sensors providing the optimum signal from each ideal location.

Figure 7:
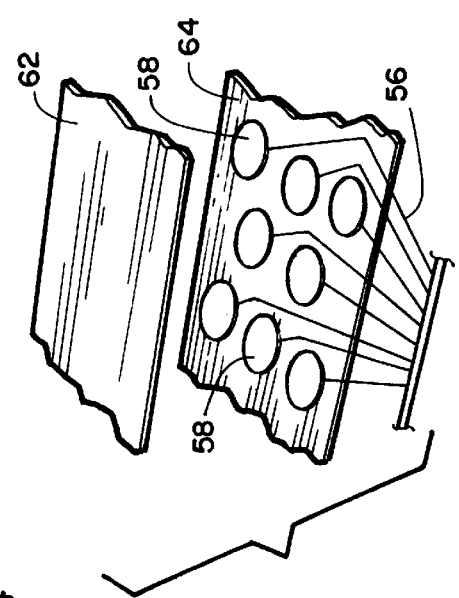
FIG. 7 is a detailed exploded view of a portion of a belt or apron showing the double wall embodiment.

While a single sheet apron 40 is useful, for optimum contact between sensors 58 and the skin of person 42, it is preferred that the apron be formed from two contiguous, coextensive, sheets, sealed together along the edges to form a closed receptacle between the sheets. Then, the receptacle may be pressurized in the manner described above to assure theat the inner sheet bearing the sensors is pressed tightly and uniformly against the skin. FIG. 7 is a detail exploded view showing the outer sheet 62 spaced from inner sheet 64, with sensors 58 attached to inner sheet 64.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. A pregnancy monitoring system, which comprises:

a belt for fitting around the abdomen of a pregnant woman and for covering substantially the entire abdomen;

said belt having two ends and means for releasably fastening said ends together to hold said belt against said abdomen;

said belt comprising two contiguous sheets sealed along edges to form a closed receptacle for covering substantially said entire abdomen;

means to direct fluid into said closed receptacle to pressurize said closed receptacle to a predetermined level against substantially said entire abdomen;

at least three panels, at least one first panel for fitting over the left side of the abdomen, at least one second panel for fitting over the right side of the abdomen and a third panel for fitting over a central area of the abdomen;

a plurality of spaced first sensors on each of said first, second and third panels, each for sensing heart beat sound;

transducer means at each said first sensor for producing first electrical signals corresponding to said sensed heart beats; and electrical means for selecting the relatively strongest first electrical signals from first sensors in each of said first, second and third panels and transmitting said strongest first electrical signals to a monitoring location.

2. The monitoring system according to claim 1 further including:

at least one second sensor on said belt for sensing uterine contractions;

transducer means at each said second sensor for producing a second electrical signal corresponding to said uterine contractions; and electrical means for transmitting said second electrical signals to said monitoring location.

3. The monitoring system according to claim 2, wherein said second sensor is a single sensor located at approximately the center of said belt so as to be at approximately the center of said abdomen when said belt is position over a woman's abdomen.

4. The monitoring system according to claim 1, wherein said electrical means includes wireless transmission means on said belt for transmitting said first and second electrical signals to a receiver at said monitoring location.

* * * * *